(12) United States Patent
van den Bosch et al.

(10) Patent No.: US 8,030,550 B2
(45) Date of Patent: Oct. 4, 2011

(54) BROCCOLI PLANTS TOLERANT TO HOLLOW/SPLIT STEM DISORDER

(75) Inventors: Franciscus van den Bosch, Kesleren (NL); Meinardus Boon, Scharwoude (NL)

(73) Assignee: Seminis Vegetable Seeds, Inc., Woodland, CA (US)

(*) Notice: Subject to any disclaimer, the term of this patent is extended or adjusted under 35 U.S.C. 154(b) by 520 days.

(21) Appl. No.: 12/152,674

(22) Filed: May 14, 2008

(65) Prior Publication Data

US 2009/0007293 A1    Jan. 1, 2009

Related U.S. Application Data

(60) Provisional application No. 60/917,872, filed on May 14, 2007.

(51) Int. Cl.
*A01H 5/00* (2006.01)
*C12N 15/82* (2006.01)

(52) U.S. Cl. .................. 800/306; 800/260; 800/278

(58) Field of Classification Search .................. None
See application file for complete search history.

(56) References Cited

U.S. PATENT DOCUMENTS

| 6,689,942 B2 | 2/2004 | Van Den Bosch et al. ... 800/306 |
|---|---|---|
| 6,784,345 B1 | 8/2004 | Barham et al. ............... 800/306 |
| 7,538,263 B2 | 5/2009 | Van Den Bosch et al. ... 800/306 |
| 2004/0117877 A1 | 6/2004 | Van Den Bosch et al. ... 800/306 |
| 2005/0262594 A1 | 11/2005 | Van Den Bosch et al. ... 800/306 |
| 2007/0118935 A1 | 5/2007 | Van Den Bosch et al. ... 800/306 |
| 2008/0078002 A1 | 3/2008 | Van Den Bosch et al. ... 800/306 |

OTHER PUBLICATIONS

DuFault, R. J Amer Soc Hort Sci 12(4):705-710, 1996.*
Cebula, S. Veg Crops Res Bull 70: 101-110, 2009.*
Qaderi et al. Env and Exp Botany 60: 428-437, 2007.*
zum Felde et al. Crop Sci 46(5): 2195-2199, 2006.*
Cutcliffe, J. Can J Plant sci 55: 867-869, 1975.*
Cutcliffe, J. Can J Plant Sci 52: 833-834, 1972.*
Shattuck et al. Can J Plant Sci 66: 683-688, 1986.*
Application for Community Plant Variety Right for Broccoli Variety BRM553916, European Community, dated Oct. 11, 2006.
Application for Community Plant Variety Right for Broccoli Variety BRM553915SI, European Community, dated Dec. 11, 2007.
Shattuck et al., "Environmental stability of yield and hollow stem in broccoli (*Brassica oleracae* var. *italica*)," *Canadian J. of Plant Sci.*, 66(3):683-688, 1986.

* cited by examiner

*Primary Examiner* — Elizabeth McElwain
(74) *Attorney, Agent, or Firm* — SNR Denton US LLP; Alissa Eagle, Esq.

(57) ABSTRACT

The invention provides broccoli seed and plants that combine high yield and quality with tolerance to hollow/split stem disorder. The invention further provides seed and plants of the broccoli lines designated BRM53-3915 and BRM53-3916 and progeny produced with at least one of these plants as a parent. The invention also relates to the plants, seeds and tissue cultures of hybrid broccoli variety RX05951180.

36 Claims, 2 Drawing Sheets

BROCCOLI PLANTS TOLERANT TO HOLLOW/SPLIT STEM DISORDER

This application claims the priority of U.S. Provisional Appl. Ser. No. 60/917,872, filed May 14, 2007, the entire disclosure of which is incorporated herein by reference.

BACKGROUND OF THE INVENTION

1. Field of the Invention

The present invention relates to the field of plant breeding and, more specifically, to the development of broccoli plants that exhibit high yield and quality combined with tolerance to hollow/split stem disorder.

2. Description of Related Art

The goal of field crop breeding is to combine various desirable traits in a single variety/hybrid. Such desirable traits may include greater yield, resistance to insects or pests, tolerance to heat and drought, better agronomic quality, higher nutritional value, growth rate and fruit properties.

Breeding techniques take advantage of a plant's method of pollination. There are two general methods of pollination: a plant self-pollinates if pollen from one flower is transferred to the same or another flower of the same plant or plant variety. A plant cross-pollinates if pollen comes to it from a flower on a different plant.

Plants that have been self-pollinated and selected for type over many generations become homozygous at almost all gene loci and produce a uniform population of true breeding progeny, a homozygous plant. A cross between two such homozygous plants of different varieties produces a uniform population of hybrid plants that are heterozygous for many gene loci. Conversely, a cross of two plants each heterozygous at a number of loci produces a population of hybrid plants that differ genetically and are not uniform. The resulting non-uniformity makes performance unpredictable.

The development of uniform varieties requires the development of homozygous inbred plants, the crossing of these inbred plants, and the evaluation of the crosses. Pedigree breeding and recurrent selection are examples of breeding methods that have been used to develop inbred plants from breeding populations. Those breeding methods combine the genetic backgrounds from two or more plants or various other broad-based sources into breeding pools from which new lines are developed by selfing and selection of desired phenotypes. The new lines are evaluated to determine which of those have commercial potential.

One crop species which has been subject to such breeding programs and is of particular value is broccoli. Broccoli possesses a compact of head of florets attached by small stems, which sprout from a thick, edible stalk. Its color can range from deep sage to dark green to purplish-green, depending upon the variety.

Broccoli has become an increasingly popular crop worldwide, especially among health-conscious consumers. An average broccoli stalk may contain only 30 calories yet provide 240% of the recommended daily allowance (RDA) of vitamin C plus 10% of the RDA of vitamin A. Broccoli is also recognized as a valuable source of dietary fiber, minerals, such as calcium and magnesium, and certain glucosinolates that may have a chemoprotective effect when consumed.

Presently, the United States is the world's largest producer of broccoli. The leading broccoli-producing states are California, Arizona, Texas and Oregon. Broccoli is also grown on a large scale in Spain, northern Europe, Central America and Australia. Of the estimated 3 billion pounds of broccoli that are marketed in the United States each year, about 1 billion pounds are minimally processed and shipped fresh, ready for consumption. The fresh broccoli market in the United States consists of two main segments: (1) whole broccoli crowns and bunch broccoli and (2) broccoli florets. A broccoli crown, e.g. of the Marathon variety, is typically a single 4 or 5 inch stalk with lateral stems trimmed off. Bunch broccoli is a group of broccoli stalks, with lateral stalks trimmed off, which are held together with a rubber band or twist tie. Florets are broccoli buds that have been trimmed from a stalk.

Broccoli is a plant of the mustard family, Brassicaceae (formerly Cruciferae). It is typically classified as the Italica Cultivar Group of the species Brassica oleracea. Other cultivar groups of Brassica oleracea include cabbage, cauliflower, kale, collard greens, kohlrabi and Brussels sprouts. A popular broccoli variety sold in North America is known as Italian green, or Calabrese, named after the Italian province of Calabria where it was first grown. Other common varieties of broccoli include Pixel, a standard variety in Japan and Australia, Marathon, a world wide standard for crowns, and Heritage, a standard for Crowns and freezers in the U.S. and Mexico.

Broccoli is a diploid species with 2N=18 chromosomes and is the result of years of breeding for the suppression of flower development in the wild mustard plant. Most broccoli varieties are cross pollinated. Much of the commercial crop is grown from F1 hybrid seeds.

While breeding efforts to date have provided a number of useful broccoli lines with beneficial traits, there remains a great need in the art for new lines with further improved traits. Such plants would benefit farmers and consumers alike by improving crop yields and/or quality.

SUMMARY OF THE INVENTION

The present invention overcomes limitations in the prior art by providing seeds and plants of broccoli lines and varieties that are tolerant to hollow stem or split stem disorder. This disorder affects many commercially significant broccoli varieties.

In certain embodiments, the present invention provides broccoli lines and varieties having complete, substantial, significant, or moderate tolerance to the hollow/split stem disorder. In some embodiments, this tolerance is such that when broccoli plants according to the invention have been cultivated to maturity less than about 0.1% of said plants have hollow or split stems. In further embodiments, the percentage of plants not displaying this disorder at maturity is less than about 1%, 3%, 5%, 10%, 15%, 20%, 25%, 30%, 35%, 40% or 50%.

In still further embodiments, the broccoli plants of the invention partly or completely resist forming hollow or split stems even when grown during climatic conditions during which this disorder is especially prevalent, for example, in broccoli types that are not tolerant to this disorder, such as Marathon. Such climatic conditions may include, for example, warm summer, warm autumn and/or plentiful water. In some aspects of the invention, the climatic conditions are those that cause a high average growth rate for broccoli plants in general or for broccoli plants of the Marathon variety in particular.

In particular embodiments, the invention provides a plant of a broccoli variety that exhibits a combination of traits comprising an individual head weighing at maturity from about 400 grams to about 600 grams and tolerance to hollow/split stem disorder. In certain embodiments, the individual head weight at maturity falls within a range, for example, having a lower value of about 400, 410, 425, 440, 455 or 475 grams, and an upper value of about 530, 545, 560, 575, 590 or 600 grams, including all ranges derivable therefrom. The term "individual head" is defined as a head of broccoli that includes a stem portion attached to the head, wherein the overall length of from the tip of the head to the end of the attached stem is about 16 cm. In some embodiments, the combination of traits may be defined as controlled by genetic means for the expression of such combination of traits found in broccoli line BRM53-3915, seed of this line having been deposited under ATCC Accession Number PTA-9181, or broccoli line BRM53-3916, seed of this line having been deposited under ATCC Accession Number PTA-8175, or a cross thereof. In other embodiments, the combination of traits may be defined as controlled by genetic means for the expression of such combination of traits found in hybrid broccoli variety RX05951180, seed of this line having been deposited under ATCC Accession Number PTA-8072, or a progeny thereof.

In further embodiments, the invention provides a head of broccoli of a plant that demonstrates tolerance to hollow or split stem, and plants producing such a trait.

The invention also provides broccoli plants comprising at least a first set of the chromosomes of broccoli line BRM53-3915 or broccoli line BRM53-3916. In one aspect, the present invention provides a broccoli plant of said line, progeny thereof, hybrid broccoli variety RX05951180 or progeny thereof. Also provided are broccoli plants having all the physiological and morphological characteristics of the broccoli line designated BRM53-3915, or the broccoli line designated BRM53-3916, or hybrid broccoli variety RX05951180. Parts of the broccoli plant of the present invention are also provided, including ovules, fruits, florets, cells or pollen of the plant.

The invention also concerns seed of broccoli line BRM53-3915, BRM53-3916, or hybrid broccoli variety RX05951180. The broccoli seed of the invention may be provided as an essentially homogeneous population of broccoli seed. Essentially homogeneous populations of seed are generally free from substantial numbers of other seed. Therefore, seed of line BRM53-3915, BRM53-3916 and/or hybrid broccoli variety RX05951180 may be defined as forming at least about 97% of the total seed, including at least about 98%, 99%, or more of the seed. In certain embodiments, the population of broccoli seed may be particularly defined as being essentially free from hybrid seed. The seed population may be separately grown to provide an essentially homogeneous population of broccoli plants designated BRM53-3915, BRM53-3916 and/or hybrid broccoli variety RX05951180.

In another aspect of the invention, a plant of broccoli line BRM53-3915 or BRM53-3916 comprising an added heritable trait is provided. The heritable trait may comprise a genetic locus that is, for example, a dominant or recessive allele. In certain embodiments of the invention, a plant of broccoli line BRM53-3915 or BRM53-3916 is defined as comprising a single locus conversion. In specific embodiments of the invention, an added genetic locus confers one or more traits such as, for example, herbicide tolerance, insect resistance, disease resistance, and modified carbohydrate metabolism. In further embodiments, the trait may be conferred by a naturally occurring gene introduced into the genome of the line by backcrossing, a natural or induced mutation, or a transgene introduced through genetic transformation techniques into the plant or a progenitor of any previous generation thereof. When introduced through transformation, a genetic locus may comprise one or more genes integrated at a single chromosomal location.

In another aspect of the invention, a tissue culture of regenerable cells of a plant of line BRM53-3915, BRM53-3916, or hybrid broccoli variety RX05951180 is provided. The tissue culture will preferably be capable of regenerating plants capable of expressing all of the physiological and morphological characteristics of the line, and of regenerating plants having substantially the same genotype as other plants of the line. Examples of some of the physiological and morphological characteristics of BRM53-3915, BRM53-3916 or RX05951180 include those traits respectively set forth in the tables herein. The regenerable cells in such tissue cultures may be derived, for example, from embryos, meristems, cotyledons, pollen, leaves, anthers, roots, root tips, pistil, flower, florets, seed and stalks. Still further, the present invention provides broccoli plants regenerated from a tissue culture of the invention, the plants having all the physiological and morphological characteristics of line(s) BRM53-3915, BRM53-3916, and/or hybrid broccoli variety RX05951180.

In yet another aspect of the invention, processes are provided for producing broccoli seeds, plants and fruit, which processes generally comprise crossing a first parent broccoli plant with a second parent broccoli plant, wherein at least one of the first or second parent broccoli plants is a plant of line BRM53-3915, BRM53-3916, or variety RX05951180. These processes may be further exemplified as processes for preparing hybrid broccoli seed or plants, wherein a first broccoli plant is crossed with a second broccoli plant of a different, distinct line to provide a hybrid that has, as one of its parents, the broccoli plant line BRM53-3915 or BRM53-3916. For example, in certain embodiments the male parent of the hybrid is a plant of line BRM53-3915 or BRM53-3916. In a further embodiment, the hybrid derived from a male parent of line BRM53-3916 is the hybrid broccoli variety designated RX05951180. In the above processes, crossing will result in the production of seed. The seed production occurs regardless of whether the seed is collected or not.

In one embodiment of the invention, the first step in "crossing" comprises planting seeds of a first and second parent broccoli plant, often in proximity so that pollination will occur for example, mediated by insect vectors. Alternatively, pollen can be transferred manually.

A second step may comprise cultivating or growing the seeds of first and second parent broccoli plants into plants that bear flowers. A third step may comprise preventing self-pollination of the plants, such as by emasculating the male portions of flowers, (i.e., treating or manipulating the flowers to produce an emasculated parent broccoli plant). Self-incompatibility systems may also be used in some hybrid crops for the same purpose. Self-incompatible plants still shed viable pollen and can pollinate plants of other varieties but are incapable of pollinating themselves or other plants of the same line.

A fourth step for a hybrid cross may comprise cross-pollination between the first and second parent broccoli plants. Yet another step comprises harvesting the seeds from at least one of the parent broccoli plants. The harvested seed can be grown to produce a broccoli plant or hybrid broccoli plant.

The present invention also provides the broccoli seeds and plants produced by a process that comprises crossing a first parent broccoli plant with a second parent broccoli plant, wherein at least one of the first or second parent broccoli plants is a plant of line BRM53-3916 or variety RX05951180. In one embodiment of the invention, broccoli seed and plants produced by the process are first generation ($F_1$) hybrid broccoli seed and plants produced by crossing a plant in accordance with the invention with another, distinct plant. In one such embodiment, the first generation ($F_1$) hybrid broccoli seed and plants produced are of the hybrid broccoli variety designated RX05951180. The present invention further contemplates plant parts of such an $F_1$ hybrid broccoli plant, and methods of use thereof. Therefore, certain exemplary embodiments of the invention provide an $F_1$ hybrid broccoli plant and seed thereof.

In still yet another aspect of the invention, the genetic complement of broccoli line BRM53-3915, BRM53-3916, and/or hybrid broccoli variety RX05951180 is provided. The phrase "genetic complement" is used to refer to the aggregate of nucleotide sequences, the expression of which sequences defines the phenotype of, in the present case, a broccoli plant, or a cell or tissue of that plant. A genetic complement thus represents the genetic makeup of a cell, tissue or plant, and a hybrid genetic complement represents the genetic make up of a hybrid cell, tissue or plant. The invention thus provides broccoli plant cells that have a genetic complement in accordance with the broccoli plant cells disclosed herein, and plants, seeds and plants containing such cells.

Plant genetic complements may be assessed by genetic marker profiles, and by the expression of phenotypic traits that are characteristic of the expression of the genetic complement, e.g., isozyme typing profiles. It is understood that line BRM53-3915, BRM53-3916, or a first generation progeny, such as hybrid broccoli variety RX05951180, thereof could be identified by any of the many well known techniques such as, for example, Simple Sequence Length Polymorphisms (SSLPs) (Williams et al., 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., 1998).

In still yet another aspect, the present invention provides hybrid genetic complements, as represented by broccoli plant cells, tissues, plants, and seeds, formed by the combination of a haploid genetic complement of a broccoli plant of the invention with a haploid genetic complement of a second broccoli plant, preferably, another, distinct broccoli plant. In another aspect, the present invention provides a broccoli plant regenerated from a tissue culture that comprises a hybrid genetic complement of this invention.

In still yet another aspect, the invention provides a method of determining the genotype of a plant of broccoli line BRM53-3915 or BRM53-3916, or hybrid broccoli variety RX05951180 comprising detecting in the genome of the plant at least a first polymorphism. The method may, in certain embodiments, comprise detecting a plurality of polymorphisms in the genome of the plant. The method may further comprise storing the results of the step of detecting the plurality of polymorphisms on a computer readable medium. The invention further provides a computer readable medium produced by such a method.

In certain embodiments, the present invention provides a method of producing broccoli comprising: (a) obtaining a plant of broccoli line BRM53-3915 or BRM53-3916 or hybrid broccoli variety RX05951180, wherein the plant has been cultivated to maturity, and (b) collecting broccoli from the plant.

In still yet another aspect, the present invention provides a method of producing a plant derived from line BRM53-3915 or BRM53-3916, or hybrid broccoli variety RX05951180, the method comprising the steps of: (a) preparing a progeny plant derived from line BRM53-3915, BRM53-3916, or hybrid broccoli variety RX05951180, wherein said preparing comprises crossing a plant of the line BRM53-3915, BRM53-3916, or hybrid broccoli variety RX05951180 with a second plant; and (b) crossing the progeny plant with itself or a second plant to produce a seed of a progeny plant of a subsequent generation. In certain embodiments, the broccoli plant of line BRM53-3915, BRM53-3916, or hybrid broccoli variety RX05951180 is the female parent. In other embodiments, the broccoli plant of line BRM53-3915, BRM53-3916 or hybrid broccoli variety RX05951180 is the male parent. In one embodiment, the plant produced is the hybrid broccoli variety designated RX05951180.

In further embodiments, the method may additionally comprise: (c) growing a progeny plant of a subsequent generation from said seed of a progeny plant of a subsequent generation and crossing the progeny plant of a subsequent generation with itself or a second plant; and repeating the steps for an additional 3-10 generations to produce a plant derived from line BRM53-3915, BRM53-3916, or hybrid broccoli variety RX05951180. The plant derived from line BRM53-3915, BRM53-3916, or hybrid broccoli variety RX05951180 may be an inbred line, and the aforementioned repeated crossing steps may be defined as comprising sufficient inbreeding to produce the inbred line. In the method, it may be desirable to select particular plants resulting from step (c) for continued crossing according to steps (b) and (c). By selecting plants having one or more desirable traits, a plant derived from line BRM53-3915, BRM53-3916, or hybrid broccoli variety RX05951180 is obtained which possesses some of the desirable traits of the line as well as potentially other selected traits.

In another aspect of the invention, a plant of hybrid broccoli variety RX05951180 comprising an added heritable trait is provided. The heritable trait may comprise a genetic locus that is a dominant or recessive allele. In specific embodiments of the invention, an added genetic locus confers one or more traits such as, for example, herbicide tolerance, insect resistance, disease resistance, and modified carbohydrate metabolism. For example, a transgene may be introduced through genetic transformation techniques into the plant.

Any embodiment discussed herein with respect to one aspect of the invention applies to other aspects of the invention as well, unless specifically noted.

The term "about" is used to indicate that a value includes the standard deviation of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or." When used in conjunction with the word "comprising" or other open language in the claims, the words "a" and "an" denote "one or more," unless specifically noted. The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits.

Other objects, features and advantages of the present invention will become apparent from the following detailed description. It should be understood, however, that the detailed description and any specific examples provided, while indicating specific embodiments of the invention, are given by way of illustration only, since various changes and modifications within the spirit and scope of the invention will become apparent to those skilled in the art from this detailed description.

DETAILED DESCRIPTION OF THE INVENTION

Figure 1:
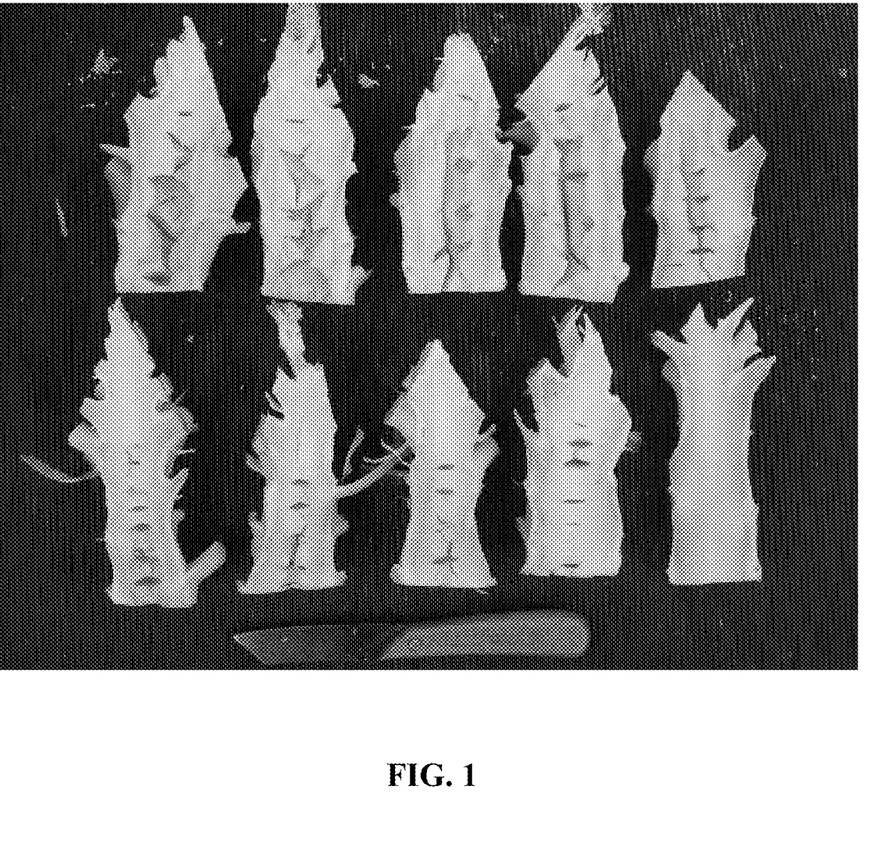
FIG. 1. Shows a vertical cross-sections of stems from a set of broccoli test crosses to demonstrate the variation in expression of 'split' or 'hollow' stem. Varieties were grown in summer/early autumn conditions at a spacing of 50×50 cm. Scoring of the characteristic is done as absent/present, i.e. all stems are scored as present, only the one on the bottom right as absent.
Figure 2:
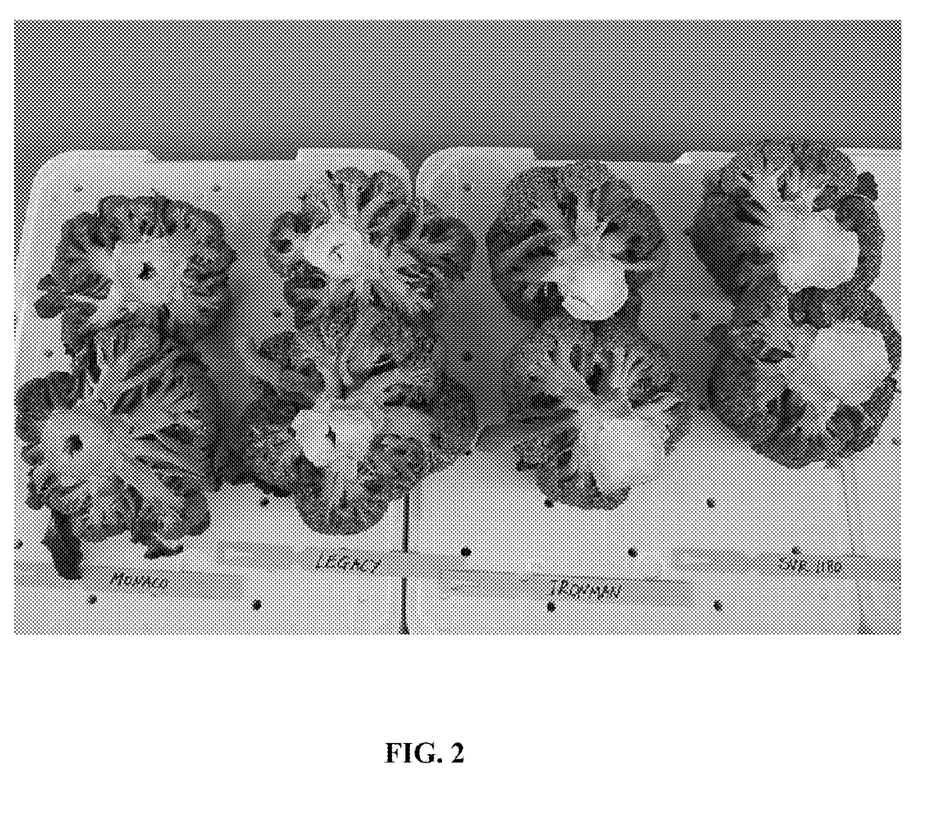
FIG. 2. Shows a horizontal cross section of stems from hybrid broccoli varieties Monaco, Legacy, Ironman and RX05951180 (designated as SVR 1180 in the figure). Varieties were grown in summer/early autumn at a spacing of 50×50 cm. In this specific trial, Ironman and RX05951180 exhibit tolerance to hollow stem.

The invention provides broccoli plants combining tolerance to hollow/split stem with other desirable traits, such as high yield and quality. It has been observed in previous lines that while certain individual inbred parent lines may show tolerance to the hollow/split stem disorder, as soon as parent lines are combined in a hybrid that produces enough heterosis to be able to produce a 400-600 g crown (a measure of yield) of sufficient quality, the tolerance is lost. What has been lacking is inbred parents that produce hybrids exhibiting substantial hollow/split stem tolerance along with other desirable traits, such as high yield and quality. Tolerance to the formation of hollow and/or split stems is an important advance because split or hollow stems spoil or declassify the product, as stems tend to turn brown or start rotting after harvest. Split or hollow stem mostly occurs during climatic conditions that support rapid growth and development of the broccoli crop; i.e. warm summer/autumn and plenty of water. Some processors also use the stem of the broccoli to mix with the broccoli florets, and split or hollow stems require extra labor to clean the stem from brown or degenerated tissue.

Hybrid RX05951180 is the first crown broccoli hybrid that combines substantial tolerance to the hollow/split stem disorder under all climatic conditions with good crown quality and high yield. RX05951180 can be classified as "Crown" broccoli according to Europe, Middle-East and Africa (EMEA) specifications requiring dome, dense curds with small uniform bead and a weight of an individual head of about 400-600 grams at maturity. The term "individual head" is defined as a head of broccoli which includes a stem portion attached to said head, wherein the overall length of from the tip of the head to the end of the attached stem is about 16 cm.

Hybrid broccoli variety RX05951180 is the outcome of 18 years of recurrent selection of types that are genetically mostly unrelated and that do not show this physiological disorder. The variety shows uniformity and stability within the limits of environmental influence for the traits described hereinafter. Sufficient seed yield of the variety is provided by the crossing of the inbred parent lines. Variety RX05951180 exhibits a number of improved traits that are described below, including the aforementioned yield, head weight at maturity and tolerance to hollow and/or split stem.

A. Origin and Breeding History

Parent line BRM53-3916 has been derived by microspore culture from line F2 DCNK2/398-1596-1. Line F2 DCNK2/398-1596-1 has been selected by pedigree selection method from F1 [DCNK2]F10×[MARATHON]DH. Hybrid RX05951180 is the product of the combination of parent line BRM53-3915 with parent line BRM53-3916.

B. Physiological and Morphological Characteristics

In accordance with one aspect of the present invention, there is provided a plant having the physiological and morphological characteristics of broccoli line BRM53-3915 or broccoli line BRM53-3916. A description of the physiological and morphological characteristics of broccoli lines BRM53-3915 and BRM53-3916 is presented in Table 1.

TABLE 1

Physiological and Morphological Characteristics of Lines BRM53-3915 and BRM53-3916*

| | Phenotype: | |
|---|---|---|
| | BRM53-3915 | BRM53-3916 |
| Plant size: | Medium | Medium |
| Stalk diameter: | Medium | Medium |
| Pose of leaves | Semi erect | Semi erect |
| Prominence of sprouting: | Sprouting (axillaries + basal) | Sprouting (axillaries + basal) |
| Leaf shape: | Elongated | Elongated |
| Leaf margin: | Undulate (wavy) | Wavy |
| Petiole wings: | Present | Present |
| Leaf color: | Blue green | Grey green |
| Leaf color intensity: | Medium | Medium |
| Blistering | Weak | Very Weak |
| Head shape in longitudinal section: | Circular | Circular |
| Head doming: | Dome | Dome |
| Head exsertion (HEX): | Within foliage | Within foliage |
| Head color: | Blue green | Grey Green |
| Head color intensity | Medium | Medium |
| Bead size | Fine | Medium |
| Earliness in specific growing season | Medium-Late | Medium-Late |

*These are typical values. Values may vary due to environment. Other values that are substantially equivalent are also within the scope of the invention.

Broccoli lines BRM53-3915 and BRM53-3916 can be reproduced by planting seeds of the line, growing the resulting broccoli plant under sib-pollinating conditions and harvesting the resulting seeds using techniques familiar to one of skill in the art.

Also in accordance with the present invention, there is provided a plant having the physiological and morphological characteristics of hybrid broccoli variety RX05951180. A description of the physiological and morphological characteristics of hybrid broccoli variety RX05951180 is presented in Table 2.

TABLE 2

Physiological and Morphological Characteristics of Variety RX05951180*

| | |
|---|---|
| Plant size: | Large |
| Stalk diameter: | Medium/large |
| Pose of leaves | Semi erect |
| Prominence of sprouting: | Sprouting (axillary + basal) |
| Leaf shape: | Elongated (medium) |
| Leaf margin: | Undulate |
| Petiole wings: | Present |
| Leaf color: | Blue green |
| Leaf color intensity: | Dark |
| Blistering | Weak |
| Head shape in longitudinal section: | Circular |
| Head doming: | High dome |
| Head exsertion (HEX): | Within foliage |

TABLE 2-continued

Physiological and Morphological Characteristics
of Variety RX05951180*

| | |
|---|---|
| Head color: | Green |
| Head color intensity | Medium dark |
| Bead size | Fine |
| Earliness in specific growing season | Late |

*These are typical values. Values may vary due to environment. Other values that are substantially equivalent are also within the scope of the invention.

Hybrid broccoli variety RX05951180 plants can be stably produced by growing the seed of the variety, such as that deposited with the ATCC.

D. Breeding Broccoli Lines BRM53-3915, BRM53-3916, and RX05951180

One aspect of the current invention concerns methods for crossing a plant of this invention with itself or a second plant and the seeds and plants produced by such methods. These methods can be used for propagation of a broccoli line, such as BRM53-3915 or BRM53-3916, or can be used to produce hybrid broccoli seeds and the plants grown therefrom. For example, hybrid seeds are produced by crossing line BRM53-3916 with second broccoli parent line. The seeds and plants of hybrid broccoli variety RX05951180 are non-limiting examples thereof.

The development of further varieties using one or more starting varieties is well known in the art. In accordance with the invention, novel varieties may be created by crossing an inbred line, e.g. BRM53-3915 or BRM53-3916, or a hybrid variety, e.g. RX05951180, of this invention followed by multiple generations of breeding according to such well known methods. New varieties may be created by crossing with any second plant. In selecting such a second plant to cross for the purpose of developing novel lines, it may be desired to choose those plants which either themselves exhibit one or more selected desirable characteristics or which exhibit the desired characteristic(s) when in hybrid combination. Once initial crosses have been made, inbreeding and selection take place to produce new varieties. For development of a uniform line, often five or more generations of selfing and selection are involved.

Uniform lines of new varieties may also be developed by way of double-haploids. This technique allows the creation of true breeding lines without the need for multiple generations of selfing and selection. In this manner true breeding lines can be produced in as little as one generation. Haploid embryos may be produced from microspores, pollen, anther cultures, or ovary cultures. The haploid embryos may then be doubled autonomously, or by chemical treatments (e.g. colchicine treatment). Alternatively, haploid embryos may be grown into haploid plants and treated to induce chromosome doubling. In either case, fertile homozygous plants are obtained. In accordance with the invention, any of such techniques may be used in connection with line BRM53-3916 and progeny thereof to achieve a homozygous line.

New varieties may be created, for example, by crossing line BRM53-3915, BRM53-3916, or hybrid variety RX05951180 with any second plant and selection of progeny in various generations and/or by doubled haploid technology. In choosing a second plant to cross for the purpose of developing novel lines, it may be desired to choose those plants which either themselves exhibit one or more selected desirable characteristics or which exhibit the desired characteristic(s) in progeny. After one or more lines are crossed, true-breeding lines may be developed.

Backcrossing can also be used to improve an inbred plant. Backcrossing transfers a specific desirable trait from one inbred or non-inbred source to an inbred that lacks that trait. This can be accomplished, for example, by first crossing a superior inbred (A) (recurrent parent) to a donor inbred (non-recurrent parent), which carries the appropriate locus or loci for the trait in question. The progeny of this cross are then mated back to the superior recurrent parent (A) followed by selection in the resultant progeny for the desired trait to be transferred from the non-recurrent parent. After five or more backcross generations with selection for the desired trait, the progeny are heterozygous for loci controlling the characteristic being transferred, but are like the superior parent for most or almost all other loci. The last backcross generation would be selfed to give pure breeding progeny for the trait being transferred.

The lines of the present invention are particularly well suited for the development of new lines based on the elite nature of the genetic background of the line. In selecting a second plant to cross with BRM53-3915, BRM53-3916, or RX05951180 for the purpose of developing novel broccoli lines, it will typically be preferred to choose those plants which either themselves exhibit one or more selected desirable characteristics or which exhibit the desired characteristic(s) when in hybrid combination. An example of a desirable characteristic is a head having a uniform deep green color and lacking in any yellowing. Further examples of desirable characteristics may include, for example: seed yield, size, shape and uniformity, floret size, shape, color and uniformity, small fine bead size, high domed heads, compact heads, smooth heads, large heads, early maturity, disease resistance, herbicide tolerance, seedling vigor, adaptability for soil conditions, adaptability for climate conditions, for example heat and/or cold tolerance, and uniform plant height.

E. Performance Characteristics of Hybrid Broccoli Variety RX05951180

As described above, variety RX05951180 exhibits desirable agronomic traits, including high yield and quality combined with tolerance to hollow/split stem disorder. Hybrid RX05951180 was first trialed during the summer and autumn. It was noticed, that RX05951180 developed no hollow stem, while other standard varieties did. Replicated trials over 2 years, in two locations (Enkhuizen and Wageningen), using two density (75×50 cm and 50×50 cm), split plot design, with 24 plants per plot of which 10 central plants were harvested when the head diameter reached about 16 cm and cut at a distance of about 16 cm from the top of the head, confirmed the earlier observations, with 4 replications. Reference varieties were Pixel, which is a standard variety in Japan and Australia, Marathon, which is a world wide standard for crowns, and Heritage, a Seminis variety, which is a standard for Crowns and freezers in US and Mexico. The results are shown in Table 4, below. In a following year, a new variety Parthenon was added to the trials. Parthenon has developed as a new standard for crown broccoli in Southern Europe. Replicated trials confirmed earlier observations, as shown in Table 5.

Legend to Tables 3 and 4: Harvest is average number of days from planting till harvest (head diameter of 16 cm); weight is average weight in grams of one head having a diameter of about 16 cm and a length of about 16 cm; hollow stem is percentage of plants having a hollow or split stem (as determined by looking at a horizontal cross section of the stems of ten plants from each plot, the horizontal cut having been made through the stem at a distance of 16 cm from top of the head of the plant); shape: 1 is flat, 3 is semi/medium dome/flat, 5 is dome; bead: 1 is very coarse/big, 3 is medium, 5 is very fine; cateyes: 1 is very many, 3 is medium, 5 is absent; GI (general impression): 1 is very poor, 9 is very good; "av." is average; "RX1180" refers to hybrid broccoli variety RX05951180.

As shown above, variety RX05951180 exhibits superior traits, which may include one or more of the following, yield (head weight), improved tolerance to hollow stem, head shape, and bead size, when compared to other lines or vari-

TABLE 3

Performance Data For Variety RX05951180

| | Harvest (dap) | | | | | | | Weight (gr/head) | | | | | | |
|---|---|---|---|---|---|---|---|---|---|---|---|---|---|---|
| | Year1 | | | | Year2 | | | Year1 | | | | Year2 | | |
| | Wag | | Enkh | | Wag | Enkh | | Wag | | Enkh | | Wag | Enkh | |
| Variety | 75 × 50 | 50 × 50 | 75 × 50 | 50 × 50 | 75 × 40 | 75 × 50 | av. | 75 × 50 | 50 × 50 | 75 × 50 | 50 × 50 | 75 × 40 | 75 × 50 | av. |
| Pixel | 56 | 61 | 51 | 57 | 56 | 58 | 57 | 594 | 420 | 415 | 458 | 450 | 385 | 454 |
| Marathon | 69 | 64 | 60 | 60 | 68 | 68 | 65 | 430 | 367 | 475 | 433 | 377 | 402 | 414 |
| Heritage | 69 | 64 | 63 | 61 | 68 | 73 | 66 | 450 | 337 | 537 | 434 | 406 | 477 | 440 |
| RX1180 | 79 | 71 | 68 | 65 | 71 | 80 | 72 | 628 | 433 | 642 | 520 | 401 | 512 | 523 |

| | Hollow stem (%) | | | | | | | Shape | | | | | | |
|---|---|---|---|---|---|---|---|---|---|---|---|---|---|---|
| | Year1 | | | | Year2 | | | Year1 | | | | Year2 | | |
| | Wag | | Enkh | | Wag | Enkh | | Wag | | Enkh | | Wag | Enkh | |
| Variety | 75 × 50 | 50 × 50 | 75 × 50 | 50 × 50 | 75 × 40 | 75 × 50 | av. | 75 × 50 | 50 × 50 | 75 × 50 | 50 × 50 | 75 × 40 | 75 × 50 | av. |
| Pixel | 23 | 0 | 48 | 10 | 63 | 19 | 27 | 3 | 1 | 1.3 | 3 | 1 | 2.8 | 2 |
| Marathon | 100 | 100 | 100 | 85 | 60 | 85 | 88 | 3.3 | 2.3 | 2.8 | 3.3 | 2.2 | 2.8 | 2.8 |
| Heritage | 100 | 100 | 98 | 98 | 93 | 100 | 98 | 3.4 | 3 | 3 | 3.3 | 1.3 | 3 | 2.8 |
| RX1180 | 13 | 7 | 8 | 3 | 0 | 32 | 11 | 5 | 5 | 5 | 4.6 | 4 | 4 | 4.6 |

| | Bead | | | | | | | Cateyes | | | | | | |
|---|---|---|---|---|---|---|---|---|---|---|---|---|---|---|
| | Year1 | | | | Year2 | | | Year1 | | | | Year2 | | |
| | Wag | | Enkh | | Wag | Enkh | | Wag | | Enkh | | Wag | Enkh | |
| Variety | 75 × 50 | 50 × 50 | 75 × 50 | 50 × 50 | 75 × 40 | 75 × 50 | av. | 75 × 50 | 50 × 50 | 75 × 50 | 50 × 50 | 75 × 40 | 75 × 50 | av. |
| Pixel | 3.8 | 4.7 | 1 | 3.4 | 1 | 2.3 | 2.7 | 5 | 4.7 | 3.3 | 5 | 1 | 2.5 | 3.6 |
| Marathon | 4 | 4.7 | 5 | 4.8 | 2.6 | 3.9 | 4.2 | 4 | 3 | 3.3 | 3.3 | 2.8 | 2.8 | 3.2 |
| Heritage | 3 | 4.7 | 2.8 | 2.8 | 1.6 | 2.8 | 3 | 3.8 | 3 | 3 | 2.8 | 2.1 | 2.4 | 2.9 |
| RX1180 | 3.8 | 5 | 5 | 4.8 | 3.9 | 2 | 4.1 | 5 | 5 | 5 | 5 | 4.1 | 3.1 | 4.5 |

| | General Impression | | | | | | |
|---|---|---|---|---|---|---|---|
| | Year1 | | | | Year2 | | |
| | Wageningen | | Enkhuizen | | Wag | Enkh | |
| Variety | 75 × 50 | 50 × 50 | 75 × 50 | 50 × 50 | 75 × 40 | 75 × 50 | average |
| Pixel | 6.8 | 5.3 | 4 | 6.5 | 2 | 3.6 | 4.7 |
| Marathon | 5.9 | 5.5 | 6.5 | 5.9 | 4.6 | 4.9 | 5.6 |
| Heritage | 5.5 | 5.3 | 5.3 | 5 | 3.5 | 3.6 | 4.7 |
| RX1180 | 7 | 7.2 | 7.8 | 7.1 | 6.9 | 5.1 | 6.9 |

TABLE 4

Summary of Further Performance Analysis For Variety RX05951180

| | Harvest (dap) | | | Weight (gr/head) | | | Hollow stem (%) | | | Shape | | | Bead | | | Cateyes | | | General Impression | | |
|---|---|---|---|---|---|---|---|---|---|---|---|---|---|---|---|---|---|---|---|---|---|
| | Wag 75 × 40 | Enkh 75 × 50 | av. | Wag 75 × 40 | Enkh 75 × 50 | av. | Wag 75 × 40 | Enkh 75 × 50 | av. | Wag 75 × 40 | Enkh 75 × 50 | av. | Wag 75 × 40 | Enkh 75 × 50 | av. | Wag 75 × 40 | Enkh 75 × 50 | av. | Wag 75 × 40 | Enkh 75 × 50 | av. |
| Variety | | | | | | | | | | | | | | | | | | | | | |
| Pixel | 56 | 58 | 57 | 450 | 385 | 418 | 63 | 19 | 41 | 1 | 2.8 | 1.9 | 1 | 2.3 | 1.7 | 1 | 2.5 | 1.8 | 2 | 3.6 | 2.8 |
| Marathon | 68 | 68 | 68 | 377 | 402 | 390 | 60 | 85 | 68 | 2.2 | 2.8 | 2.5 | 2.6 | 3.9 | 3.3 | 2.8 | 2.8 | 2.8 | 4.6 | 4.9 | 4.8 |
| Heritage | 68 | 73 | 71 | 406 | 477 | 442 | 93 | 100 | 97 | 1.3 | 3 | 2.2 | 1.6 | 2.8 | 2.2 | 2.1 | 2.4 | 2.3 | 3.5 | 3.6 | 3.6 |
| Parthenon | 68 | 74 | 71 | 432 | 499 | 466 | 48 | 100 | 74 | 3.3 | 3.6 | 3.5 | 3.6 | 3.6 | 3.6 | 3.5 | 2.9 | 3.2 | 6.5 | 4.8 | 5.7 |
| RX1180 | 71 | 80 | 76 | 401 | 512 | 457 | 0 | 32 | 16 | 4 | 4 | 4 | 3.9 | 2 | 3 | 4.1 | 3.1 | 3.6 | 6.9 | 5.1 | 6 | eties. One important aspect of the invention thus provides seed of the variety for commercial use.

G. Further Embodiments of the Invention

When the term broccoli plant is used in the context of the present invention, this also includes plants modified to include at least a first desired heritable trait. Such plants may, in one embodiment, be developed by a plant breeding technique called backcrossing, wherein essentially all of the desired morphological and physiological characteristics of a variety are recovered in addition to a genetic locus transferred into the plant via the backcrossing technique. The term single locus converted plant as used herein refers to those broccoli plants which are developed by a plant breeding technique called backcrossing, wherein essentially all of the desired morphological and physiological characteristics of a variety are recovered in addition to the single locus transferred into the variety via the backcrossing technique.

Backcrossing methods can be used with the present invention to improve or introduce a characteristic into the present variety. The parental broccoli plant which contributes the locus for the desired characteristic is termed the nonrecurrent or donor parent. This terminology refers to the fact that the nonrecurrent parent is used one time in the backcross protocol and therefore does not recur. The parental broccoli plant to which the locus or loci from the nonrecurrent parent are transferred is known as the recurrent parent as it is used for several rounds in the backcrossing protocol.

In a typical backcross protocol, the original variety of interest (recurrent parent) is crossed to a second variety (nonrecurrent parent) that carries the single locus of interest to be transferred. The resulting progeny from this cross are then crossed again to the recurrent parent and the process is repeated until a broccoli plant is obtained wherein essentially all of the desired morphological and physiological characteristics of the recurrent parent are recovered in the converted plant, in addition to the single transferred locus from the nonrecurrent parent.

The selection of a suitable recurrent parent is an important step for a successful backcrossing procedure. The goal of a backcross protocol is to alter or substitute a single trait or characteristic in the original variety. To accomplish this, a single locus of the recurrent variety is modified or substituted with the desired locus from the nonrecurrent parent, while retaining essentially all of the rest of the desired genetic, and therefore the desired physiological and morphological constitution of the original variety. The choice of the particular nonrecurrent parent will depend on the purpose of the backcross; one of the major purposes is to add some commercially desirable trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

In one embodiment, progeny broccoli plants of a backcross in which BRM53-3915 or BRM53-3916 is the recurrent parent comprise (i) the desired trait from the non-recurrent parent and (ii) all of the physiological and morphological characteristics of broccoli line BRM53-3915 or BRM53-3916 as determined at the 5% significance level when grown in the same environmental conditions.

Broccoli varieties can also be developed from more than two parents. The technique, known as modified backcrossing, uses different recurrent parents during the backcrossing. Modified backcrossing may be used to replace the original recurrent parent with a variety having certain more desirable characteristics or multiple parents may be used to obtain different desirable characteristics from each.

Many single locus traits have been identified that are not regularly selected for in the development of a new inbred but that can be improved by backcrossing techniques. Single locus traits may or may not be transgenic; examples of these traits include, but are not limited to, male sterility, herbicide tolerance, resistance to bacterial, fungal, or viral disease, insect resistance, restoration of male fertility, modified fatty acid or carbohydrate metabolism, and enhanced nutritional quality. These comprise genes generally inherited through the nucleus.

Direct selection may be applied where the single locus acts as a dominant trait. An example of a dominant trait is the anthracnose resistance trait. For this selection process, the progeny of the initial cross are sprayed with anthracnose spores prior to the backcrossing. The spraying eliminates any plants which do not have the desired anthracnose resistance characteristic, and only those plants which have the anthracnose resistance gene are used in the subsequent backcross. This process is then repeated for all additional backcross generations.

Selection of broccoli plants for breeding is not necessarily dependent on the phenotype of a plant and instead can be based on genetic investigations. For example, one can utilize a suitable genetic marker which is closely genetically linked to a trait of interest. One of these markers can be used to identify the presence or absence of a trait in the offspring of a particular cross, and can be used in selection of progeny for continued breeding. This technique is commonly referred to as marker assisted selection. Any other type of genetic marker or other assay which is able to identify the relative presence or absence of a trait of interest in a plant can also be useful for breeding purposes. Procedures for marker assisted selection applicable to the breeding of broccoli are well known in the art. Such methods will be of particular utility in the case of recessive traits and variable phenotypes, or where conventional assays may be more expensive, time consuming or otherwise disadvantageous. Types of genetic markers which could be used in accordance with the invention include, but are not necessarily limited to, Simple Sequence Length Polymorphisms (SSLPs) (Williams et al., 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., 1998).

H. Plants Derived by Genetic Engineering

Many useful traits that can be introduced by backcrossing, as well as directly into a plant, are those which are introduced by genetic transformation techniques. Genetic transformation may therefore be used to insert a selected transgene into the hybrid broccoli variety of the invention, and/or a parent of the hybrid broccoli line of the invention, or may, alternatively, be used for the preparation of transgenes which can be introduced by backcrossing. Methods for the transformation of plants, including broccoli, are well known to those of skill in the art. For example, Cao et al. (1999), disclose one method of generation of transgenic broccoli.

As discussed by Puddephat et al. (1996), gene transfer into cultivated forms of *B. oleracea* such as broccoli requires reproducible and efficient methods for genetic transformation and plant regeneration. Most research efforts have been directed at developing *Agrobacterium*-mediated transformation methods with relatively little emphasis on direct gene transfer techniques. Common procedures for the transformation of *B. oleracea* have not emerged, due in large part to the inherent variability between and amongst genotypes. The principal difficulties relate to combining efficient plant regeneration with gene transfer. Inefficient selection can result in the regeneration of chimeric plants upon *Agrobacterium turnefaciens*-mediated transformation. Promising results have been obtained with *Agrobacterium rhizogenes*-mediated transformation. Few agronomically useful characters have been introduced, the majority of research having been confined to the introduction of marker and reporter genes.

Generally speaking, techniques which may be employed for the genetic transformation of broccoli include, but are not limited to, electroporation, microprojectile bombardment, *Agrobacterium*-mediated transformation and direct DNA uptake by protoplasts. For a review of transformation techniques relating to broccoli, see, e.g., Earle et al. (1996); Puddephat et al. (1996).

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

A particularly efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate. This technique has been utilized to transform broccoli for the transient expression of the β-glucuronidase gene, for example (Puddephat et al., 1999).

An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target broccoli cells. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large.

Microprojectile bombardment techniques are widely applicable, and may be used to transform virtually any plant species. An example of using this technique with broccoli is presented in U.S. Pat. No. 6,297,056.

*Agrobacterium*-mediated transfer is another widely applicable system for introducing gene loci into plant cells. An advantage of the technique is that DNA can be introduced into whole plant tissues, thereby bypassing the need for regeneration of an intact plant from a protoplast. Modern *Agrobacterium* transformation vectors are capable of replication in *E. coli* as well as *Agrobacterium*, allowing for convenient manipulations (Klee et al., 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, *Agrobacterium* containing both armed and disarmed Ti genes can be used for transformation.

In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells is well known in the art (Fraley et al., 1985; U.S. Pat. No. 5,563,055). Examples of using *Agrobacterium*-mediated transformation of broccoli include those found in U.S. Pat. Nos. 6,043,409 and 5,998,702.

Transformation of plant protoplasts also can be achieved using methods based on calcium phosphate precipitation, polyethylene glycol treatment, electroporation, and combinations of these treatments (see, e.g., Potrykus et al., 1985; Omirulleh et al., 1993; Fromm et al., 1986; Uchimiya et al., 1986; Marcotte et al., 1988). Transformation of plants and expression of foreign genetic elements is exemplified in Choi et al. (1994), and Ellul et al. (2003).

A number of promoters have utility for plant gene expression for any gene of interest including but not limited to selectable markers, scoreable markers, genes for pest tolerance, disease resistance, nutritional enhancements and any other gene of agronomic interest. Examples of constitutive promoters useful for broccoli plant gene expression include, but are not limited to, the cauliflower mosaic virus (CaMV) P-35S promoter, which confers constitutive, high-level expression in most plant tissues (see, e.g., Odel et al., 1985), including monocots (see, e.g., Dekeyser et al., 1990; Terada and Shimamoto, 1990); a tandemly duplicated version of the CaMV 35S promoter, the enhanced 35S promoter (P-e35S) the nopaline synthase promoter (An et al., 1988), the octopine synthase promoter (Fromm et al.,); and the figwort mosaic virus (P-FMV) promoter as described in U.S. Pat. No. 5,378,619 and an enhanced version of the FMV promoter (P-eFMV) where the promoter sequence of P-FMV is duplicated in tandem, the cauliflower mosaic virus 19S promoter, a sugarcane bacilliform virus promoter, a commelina yellow mottle virus promoter, and other plant DNA virus promoters known to express in plant cells.

A variety of plant gene promoters that are regulated in response to environmental, hormonal, chemical, and/or developmental signals can be used for expression of an operably linked gene in plant cells, including promoters regulated by (1) heat (Callis et al., 1988), (2) light (e.g., pea rbcS-3A promoter, Kuhlemeier et al., 1989; maize rbcS promoter, Schaffner and Sheen, 1991; or chlorophyll a/b-binding protein promoter, Simpson et al., 1985), (3) hormones, such as abscisic acid (Marcotte et al., 1989), (4) wounding (e.g., wun1, Siebertz et al., 1989); or (5) chemicals such as methyl jasmonate, salicylic acid, or Safener. It may also be advantageous to employ organ-specific promoters (e.g., Roshal et al., 1987; Schernthaner et al., 1988; Bustos et al., 1989).

Exemplary nucleic acids which may be introduced to the broccoli lines or varieties of this invention include, for example, DNA sequences or genes from another species, or even genes or sequences which originate with or are present in the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a broccoli plant according to the invention. Non-limiting examples of particular genes and corresponding phenotypes one may choose to introduce into a broccoli plant include one or more genes for insect tolerance, such as a *Bacillus thuringiensis* (Bt) gene, pest tolerance such as genes for fungal disease control, herbicide tolerance such as genes conferring glyphosate tolerance, and genes for quality improvements such as yield, nutritional enhancements, environmental or stress tolerances, or any desirable changes in plant physiology, growth, development, morphology or plant product(s). For example, structural genes would include any gene that confers insect tolerance including but not limited to a Bacillus insect control protein gene as described in WO 99/31248, herein incorporated by reference in its entirety, U.S. Pat. No. 5,689,052, herein incorporated by reference in its entirety, U.S. Pat. Nos. 5,500,365 and 5,880,275, herein incorporated by reference it their entirety. In another embodiment, the structural gene can confer tolerance to the herbicide glyphosate as conferred by genes including, but not limited to *Agrobacterium* strain CP4 glyphosate tolerant EPSPS gene (aroA:CP4) as described in U.S. Pat. No. 5,633,435, herein incorporated by reference in its entirety, or glyphosate oxidoreductase gene (GOX) as described in U.S. Pat. No. 5,463,175, herein incorporated by reference in its entirety.

Alternatively, the DNA coding sequences can affect these phenotypes by encoding a non-translatable RNA molecule that causes the targeted inhibition of expression of an endogenous gene, for example via antisense- or cosuppression-mediated mechanisms (see, for example, Bird et al., 1991). The RNA could also be a catalytic RNA molecule (i.e., a ribozyme) engineered to cleave a desired endogenous mRNA product (see for example, Gibson and Shillito, 1997). Thus, any gene which produces a protein or mRNA which expresses a phenotype or morphology change of interest is useful for the practice of the present invention.

I. Definitions

In the description and tables herein, a number of terms are used. In order to provide a clear and consistent understanding of the specification and claims, the following definitions are provided:

Allele: Any of one or more alternative forms of a gene locus, all of which alleles relate to one trait or characteristic. In a diploid cell or organism, the two alleles of a given gene occupy corresponding loci on a pair of homologous chromosomes.

Backcrossing: A process in which a breeder repeatedly crosses hybrid progeny, for example a first generation hybrid ($F_1$), back to one of the parents of the hybrid progeny. Backcrossing can be used to introduce one or more single locus conversions from one genetic background into another.

Crossing: The mating of two parent plants.

Cross-pollination: Fertilization by the union of two gametes from different plants.

Diploid: A cell or organism having two sets of chromosomes.

Emasculate: The removal of plant male sex organs or the inactivation of the organs with a cytoplasmic or nuclear genetic factor conferring male sterility or a chemical agent.

Enzymes: Molecules which can act as catalysts in biological reactions.

$F_1$ Hybrid: The first generation progeny of the cross of two nonisogenic plants.

Genotype: The genetic constitution of a cell or organism.

Haploid: A cell or organism having one set of the two sets of chromosomes in a diploid.

Linkage: A phenomenon wherein alleles on the same chromosome tend to segregate together more often than expected by chance if their transmission was independent.

Marker: A readily detectable phenotype, preferably inherited in codominant fashion (both alleles at a locus in a diploid heterozygote are readily detectable), with no environmental variance component, i.e., heritability of 1.

Phenotype: The detectable characteristics of a cell or organism, which characteristics are the manifestation of gene expression.

Quantitative Trait Loci (QTL): Quantitative trait loci (QTL) refer to genetic loci that control to some degree numerically representable traits that are usually continuously distributed.

Regeneration: The development of a plant from tissue culture.

Resistance: As used herein, the terms "resistance" and "tolerance" are used interchangeably to describe plants that show no symptoms to a specified biotic pest, pathogen, abiotic influence or environmental condition. These terms are also used to describe plants showing some symptoms but that are still able to produce marketable product with an acceptable yield. Some plants that are referred to as resistant or tolerant are only so in the sense that they may still produce a crop, even though the plants are stunted and the yield is reduced.

Self-pollination: The transfer of pollen from the anther to the stigma of the same plant.

Single Locus Converted (Conversion) Plant: Plants which are developed by a plant breeding technique called backcrossing, wherein essentially all of the desired morphological and physiological characteristics of a broccoli variety are recovered in addition to the characteristics of the single locus transferred into the variety via the backcrossing technique and/or by genetic transformation.

Substantially Equivalent: A characteristic that, when compared, does not show a statistically significant difference (e.g., $p=0.05$) from the mean.

Tetraploid: A cell or organism having four sets of chromosomes.

Tissue Culture: A composition comprising isolated cells of the same or a different type or a collection of such cells organized into parts of a plant.

Transgene: A genetic locus comprising a sequence which has been introduced into the genome of a broccoli plant by transformation.

Triploid: A cell or organism having three sets of chromosomes.

J. Deposit Information

Deposits of broccoli line BRM53-3915, BRM53-3916 and hybrid broccoli variety RX05951180, which are disclosed above and recited in the claims, have been made with the American Type Culture Collection (ATCC), 10801 University Blvd., Manassas, Va. 20110-2209. The date of deposit was May 2, 2008 for broccoli line BRM53-3915, Jan. 24, 2007 for broccoli line BRM53-3916 and Dec. 11, 2006 for hybrid broccoli variety RX05951180. The accession number for the deposited seeds of broccoli line BRM53-3916 is ATCC Accession No. PTA-8175. The accession number for the deposited seeds of broccoli line BRM53-3915 is ATCC Accession No. PTA-9181. The accession number for the deposited seeds of broccoli variety RX05951180 is ATCC Accession No. PTA-8072. Upon issuance of a patent, all restrictions upon the deposits will be removed, and the deposits are intended to meet all of the requirements of 37 C.F.R. §1.801-1.809. The deposits will be maintained in the depository for a period of 30 years, or 5 years after the last request, or for the effective life of the patent, whichever is longer, and will be replaced if necessary during that period.

Although the foregoing invention has been described in some detail by way of illustration and example for purposes of clarity and understanding, it will be obvious that certain changes and modifications may be practiced within the scope of the invention, as limited only by the scope of the appended claims.

All references cited herein are hereby expressly incorporated herein by reference.

REFERENCES

The following references, to the extent that they provide exemplary procedural or other details supplementary to those set forth herein, are specifically incorporated herein by reference:

U.S. Pat. No. 5,378,619
U.S. Pat. No. 5,463,175
U.S. Pat. No. 5,500,365
U.S. Pat. No. 5,563,055
U.S. Pat. No. 5,633,435
U.S. Pat. No. 5,689,052
U.S. Pat. No. 5,880,275
U.S. Pat. No. 5,998,702
U.S. Pat. No. 6,043,409
U.S. Pat. No. 6,297,056
An et al., *Plant Physiol.*, 88:547, 1988.
Bird et al., *Biotech. Gen. Engin. Rev.*, 9:207, 1991.
Bustos et al., *Plant Cell*, 1:839, 1989.
Callis et al., *Plant Physiol.*, 88:965, 1988.
Cao et al., *Mol. Breeding*, 5:131-141, 1999.
Choi et al., *Plant Cell Rep.*, 13: 344-348, 1994.
Dekeyser et al., *Plant Cell*, 2:591, 1990.
Earle et al., *Acta Hort. (ISHS)*, 407:161-168, 1996.
Ellul et al., *Theor. Appl. Genet.*, 107:462-469, 2003.
EP 534 858
Fraley et al., *Bio/Technology*, 3:629-635, 1985.
Fromm et al., *Nature*, 312:791-793, 1986.
Fromm et al., *Plant Cell*, 1:977, 1989.
Gibson and Shillito, *Mol. Biotech.*, 7:125, 1997
Klee et al., *Bio-Technology*, 3(7):637-642, 1985.
Kuhlemeier et al., *Plant Cell*, 1:471, 1989.
Marcotte et al., *Nature*, 335:454, 1988.
Marcotte et al., *Plant Cell*, 1:969, 1989.
Odel et al., *Nature*, 313:810, 1985.
Omirulleh et al., *Plant Mol. Biol.*, 21(3):415-428, 1993.
Potrykus et al., *Mol. Gen. Genet.*, 199:183-188, 1985.
Puddephat et al., *J. Hort. Sci. Biotech.*, 74:714-720, 1990.
Puddephat et al., *Mol. Breeding*, 2:185-210, 1996.
Roshal et al., *EMBO J.*, 6:1155, 1987.
Schaffner and Sheen, *Plant Cell*, 3:997, 1991.
Schernthaner et al., *EMBO J.*, 7:1249, 1988.
Siebertz et al., *Plant Cell*, 1:961, 1989.
Simpson et al., *EMBO J.*, 4:2723, 1985.
Terada and Shimamoto, *Mol. Gen. Genet.*, 220:389, 1990.
Uchimiya et al., *Mol. Gen. Genet.*, 204:204, 1986.
Wang et al., *Science*, 280:1077-1082, 1998.
Williams et al., *Nucleic Acids Res.*, 1 8:6531-6535, 1990.
WO 99/31248

What is claimed is:

1. A broccoli plant comprising at least a first set of the chromosomes of broccoli line BRM53-3915 or broccoli line BRM53-3916, a sample of seed of said broccoli lines BRM53-3915 and BRM53-3916 having been deposited under ATCC Accession Numbers PTA-9181 and PTA-8175, respectively.

2. The broccoli plant of claim 1, wherein the plant expresses all of the physiological and morphological characteristics of hybrid broccoli variety RX05951180, a sample of seed of said variety having been deposited under ATCC Accession Number PTA-8072.

3. The broccoli plant of claim 1, comprising at least a first set of the chromosomes of broccoli line BRM53-3915, a sample of seed of said broccoli line BRM53-3915 having been deposited under ATCC Accession Number PTA-9181.

4. The broccoli plant of claim 1, comprising at least a first set of the chromosomes of broccoli line BRM53-3916, a sample of seed of said broccoli line BRM53-3916 having been deposited under ATCC Accession Number PTA-8175.

5. A seed of broccoli line BRM53-3915 or BRM53-3916, a sample of seed of said broccoli lines BRM53-3915 and BRM53-3916 having been deposited under ATCC Accession Numbers PTA-9181 and PTA-8175, respectively.

6. A plant grown from the seed of claim 5.

7. A plant part of the plant of claim 6.

8. The plant part of claim 7, further defined as a leaf, a floret, an ovule, pollen, a cell or a head of broccoli.

9. A broccoli plant, or a part thereof, having all the physiological and morphological characteristics of the broccoli plant of claim 6.

10. A tissue culture of regenerable cells of broccoli line BRM53-3915 or broccoli line BRM53-3916, a sample of seed of said broccoli lines BRM53-3915 and BRM53-3916 having been deposited under ATCC Accession Numbers PTA-9181 and PTA-8175, respectively.

11. The tissue culture according to claim 10, comprising cells or protoplasts from a plant part selected from the group consisting of embryos, meristems, cotyledons, pollen, leaves, anthers, roots, root tips, pistil, flower, florets, seed and stalks.

12. A broccoli plant regenerated from the tissue culture of claim 10, wherein the regenerated plant expresses all of the physiological and morphological characteristics of broccoli line BRM53-3915 or broccoli line BRM53-3916, a sample of seed of said broccoli lines BRM53-3915 and BRM53-3916 having been deposited under ATCC Accession Numbers PTA-9181 and PTA-8175, respectively.

13. A method of vegetatively propagating a plant of broccoli line BRM53-3915 or broccoli line BRM53-3916 comprising the steps of:
    (a) collecting tissue capable of being propagated from a plant of broccoli line BRM53-3915 or broccoli line BRM53-3916, a sample of seed of said broccoli lines BRM53-3915 and BRM53-3916 having been deposited under ATCC Accession Numbers PTA-9181 and PTA-8175, respectively;
    (b) cultivating said tissue to obtain proliferated shoots; and
    (c) rooting said proliferated shoots to obtain rooted plantlets.

14. The method of claim 13, further comprising growing plants from said rooted plantlets.

15. A method of introducing a desired trait into broccoli line BRM53-3915 or broccoli line BRM53-3916 comprising:
  (a) crossing a plant of line BRM53-3915 or BRM53-3916 with a second broccoli plant that comprises a desired trait to produce F1 progeny, wherein a sample of seed of said broccoli lines BRM53-3915 and BRM53-3916 has been deposited under ATCC Accession Numbers PTA-9181 and PTA-8175, respectively;
  (b) selecting an F1 progeny that comprises the desired trait;
  (c) crossing the selected F1 progeny with a plant of line BRM53-3915 or BRM53-3916 to produce backcross progeny;
  (d) selecting backcross progeny comprising the desired trait and the physiological and morphological characteristic of broccoli line BRM53-3915 or BRM53-3916; and
  (e) repeating steps (c) and (d) three or more times in succession to produce selected fourth or higher backcross progeny that comprise the desired trait.

16. A broccoli plant produced by the method of claim 15.

17. A method of producing a plant of broccoli line BRM53-3915 or broccoli line BRM53-3916 comprising an added desired trait, the method comprising introducing a transgene conferring the desired trait into a plant of broccoli line BRM53-3915 or BRM53-3916, wherein a sample of seed of said broccoli lines BRM53-3915 and BRM53-3916 has been deposited under ATCC Accession Numbers PTA-9181 and PTA-8175, respectively.

18. A method for producing a seed of a line BRM53-3915-derived or BRM53-3916-derived broccoli plant comprising the steps of:
  (a) crossing a broccoli plant of line BRM53-3915 or BRM53-3916 with a second broccoli plant, wherein a sample of seed of said broccoli lines BRM53-3915 and BRM53-3916 has been deposited under ATCC Accession Numbers PTA-9181 and PTA-8175, respectively; and
  (b) allowing seed of a BRM53-3915-derived or BRM53-3916-derived broccoli plant to form.

19. The method of claim 18, further comprising the steps of:
  (c) crossing a plant grown from said BRM53-3915-derived or BRM53-3916-derived broccoli seed with itself or a second broccoli plant to yield additional BRM53-3915-derived or BRM53-3916-derived broccoli seed;
  (d) growing said additional BRM53-3915-derived or BRM53-3916-derived broccoli seed of step (c) to yield additional BRM53-3915-derived or BRM53-3916-derived broccoli plants; and
  (e) repeating the crossing and growing steps of (c) and (d) to generate further BRM53-3915-derived or BRM53-3916-derived broccoli plants.

20. The method of claim 18, wherein the second broccoli plant is of an inbred broccoli line.

21. An F1 hybrid seed having a plant of line BRM53-3915 or line BRM53-3916 as one parent.

22. The F1 hybrid seed of claim 21, wherein line BRM53-3915 or line BRM53-3916 is a male parent.

23. The F1 hybrid seed of claim 21, wherein line BRM53-3915 or line BRM53-3916 is a female parent.

24. The F1 hybrid seed of claim 22, wherein the F1 hybrid seed is produced by crossing a plant of said line BRM53-3915 or line BRM53-3916 as a male parent with a second broccoli plant used as a female parent that is male sterile.

25. A plant produced by growing the seed of claim 21.

26. The plant of claim 25, wherein the plant is of hybrid broccoli variety RX05951180, a sample of seed of said variety having been deposited under ATCC Accession Number PTA-8072.

27. A plant part of the plant of claim 26.

28. The plant part of claim 27, further defined as a leaf, a floret, an ovule, pollen, a cell or a head of broccoli.

29. A tissue culture of cells of the plant of claim 26.

30. The tissue culture of claim 29, wherein cells of the tissue culture are from a tissue selected from the group consisting of embryos, meristems, cotyledons, pollen, leaves, anthers, roots, root tips, pistil, flower, florets, seed and stalks.

31. A broccoli plant regenerated from the tissue culture of claim 29, wherein the regenerated plant expresses all of the physiological and morphological characteristics of hybrid broccoli variety RX05951180, a sample of seed of said variety having been deposited under ATCC Accession Number PTA-8072.

32. The seed of claim 25, wherein one or both of the plant of line BRM53-3915 or line BRM53-3916 and the second plant further comprises a transgene.

33. The seed of claim 25, wherein one or both of the plant of line BRM53-3915 or line BRM53-3916 and the second plant comprises a single locus conversion.

34. A method of vegetatively propagating a plant of hybrid broccoli variety RX05951180, a sample of seed of said hybrid having been deposited under ATCC Accession Number PTA-8072, the method comprising the steps of:
  (a) collecting tissue capable of being propagated from the plant of claim 26;
  (b) cultivating said tissue to obtain proliferated shoots; and
  (c) rooting said proliferated shoots to obtain rooted plantlets.

35. The method of claim 34, further comprising growing plants from said rooted plantlets.

36. A method of producing broccoli comprising:
  (a) obtaining the plant of claim 26, wherein the plant has been cultivated to maturity; and
  (b) collecting broccoli from the plant.

* * * * *